United States Patent [19]
Shartle

[11] Patent Number: 6,084,660
[45] Date of Patent: Jul. 4, 2000

[54] INITIATION OF AN ANALYTICAL MEASUREMENT IN BLOOD

[75] Inventor: Robert Justice Shartle, Livermore, Calif.

[73] Assignee: Lifescan, Inc., Milpitas, Calif.

[21] Appl. No.: 09/354,995

[22] Filed: Jul. 16, 1999

Related U.S. Application Data

[60] Provisional application No. 60/093,421, Jul. 20, 1998.

[51] Int. Cl.[7] .......................... G01N 33/48; G01N 33/86; G01N 21/03
[52] U.S. Cl. .................................. 356/39; 436/8; 436/52; 436/63; 356/246; 356/427
[58] Field of Search .............................. 356/39, 40, 427, 356/246; 436/8, 52, 63, 164

[56] References Cited

U.S. PATENT DOCUMENTS

| | | | |
|---|---|---|---|
| 3,620,676 | 11/1971 | Davis | 23/253 |
| 3,640,267 | 2/1972 | Hurtig et al. | 128/2 |
| 4,088,448 | 5/1978 | Lilja et al. | 23/259 |
| 4,426,451 | 1/1984 | Columbus | 436/518 |
| 4,822,568 | 4/1989 | Tomita | 422/73 |
| 4,868,129 | 9/1989 | Gibbons et al. | 436/179 |
| 5,230,866 | 7/1993 | Shartle et al. | 422/103 |
| 5,472,603 | 12/1995 | Schembri | 210/380 |
| 5,627,041 | 5/1997 | Shartle | 435/7.24 |
| 5,700,695 | 12/1997 | Yassinzadeh et al. | 436/180 |
| 5,736,404 | 4/1998 | Yassinzadeh et al. | 436/52 |

FOREIGN PATENT DOCUMENTS

| | | | |
|---|---|---|---|
| 0 803 288 | 10/1997 | European Pat. Off. | B01L 3/00 |
| 0 922 954 A2 | 6/1999 | European Pat. Off. | G01N 21/86 |
| WO 94/02850 | 2/1994 | WIPO | G01N 33/53 |

*Primary Examiner*—Frank G. Font
*Assistant Examiner*—Layla Lauchman
*Attorney, Agent, or Firm*—James Riesenfeld

[57] ABSTRACT

A distinctive optical signature permits a fluidic medical diagnostic device to measure an analyte concentration or a property of whole blood, particularly the coagulation time, only after first insuring that a whole blood sample has been introduced into the device. A suitable device has at one end a sample port for introducing a sample and at the other end a bladder for drawing the sample to a measurement area. By requiring a meter, used in conjunction with the device, to first detect the distinctive optical signature, a sample is drawn to the measurement area only if it is whole blood. In that case, a channel carries the sample from the sample port to the measurement area, and a stop junction, between the measurement area and bladder, halts the sample flow. The meter measures a physical property of the blood sample—typically, optical transmittance—after it has interacted with a reagent in the measurement area.

5 Claims, 8 Drawing Sheets

INITIATION OF AN ANALYTICAL MEASUREMENT IN BLOOD

CROSS-REFERENCE TO PRIOR PROVISIONAL APPLICATION

This application claims the benefit of U.S. Provisional Application No. 60/093,421, filed Jul. 20, 1998.

BACKGROUND OF THE INVENTION

1. Field of the Invention

This invention relates to a fluidic medical diagnostic device for measuring the concentration of an analyte in or a property of a biological fluid; more particularly, to a method for initiating such a measurement when the fluid exhibits certain characteristics.

2. Description of the Related Art

A variety of medical diagnostic procedures involve tests on biological fluids, such as blood, urine, or saliva, and are based on a change in a physical characteristic of such a fluid or an element of the fluid, such as blood serum. The characteristic can be an electrical, magnetic, fluidic, or optical property. When an optical property is monitored, these procedures may make use of a transparent or translucent device to contain the biological fluid and a reagent. A change in light absorption of the fluid can be related to an analyte concentration in, or property of, the fluid. Typically, a light source is located adjacent to one surface of the device and a detector is adjacent to the opposite surface. The detector measures light transmitted through a fluid sample. Alternatively, the light source and detector can be on the same side of the device, in which case the detector measures light scattered and/or reflected by the sample. Finally, a reflector may be located at or adjacent to the opposite surface. A device of this latter type, in which light is first transmitted through the sample area, then reflected through a second time, is called a "transflectance" device. References to "light" throughout this specification and the appended claims should be understood to include the infrared and ultraviolet spectra, as well as the visible. References to "absorption" are meant to refer to the reduction in intensity as a light beam passes through a medium; thus, it encompasses both "true" absorption and scattering.

An example of a transparent test device is described in Wells et al. WO94/02850, published on Feb. 3, 1994. Their device comprises a sealed housing, which is transparent or translucent, impervious, and rigid or semi-rigid. An assay material is contained within the housing, together with one or more assay reagents at predetermined sites. The housing is opened and the sample introduced just before conducting the assay. The combination of assay reagents and analyte in the sample results in a change in optical properties, such as color, of selected reagents at the end of the assay. The results can be read visually or with an optical instrument.

U.S. Pat. No. 3,620,676, issued on Nov. 16, 1971 to Davis, discloses a colorimetric indicator for liquids. The indicator includes a "half-bulb cavity", which is compressible. The bulb is compressed and released to form a suction that draws fluid from a source, through a half-tubular cavity that has an indicator imprinted on its wall. The only controls on fluid flow into the indicator are how much the bulb is compressed and how long the indicator inlet is immersed in the source, while the bulb is released.

U.S. Pat. No. 3,640,267, issued on Feb. 8, 1972 to Hurtig et al., discloses a container for collecting samples of body fluid that includes a chamber that has resilient, collapsible walls. The walls are squeezed before the container inlet is placed into the fluid being collected. When released, the walls are restored to their uncollapsed condition, drawing fluid into and through the inlet. As with the Davis device, discussed above, control of fluid flow into the indicator is very limited.

U.S. Pat. No. 4,088,448, issued on May 9, 1978 to Lilja et al., discloses a cuvette, which permits optical analysis of a sample mixed with a reagent. The reagent is coated on the walls of a cavity, which is then filled with a liquid sample. The sample mixes with the reagent to cause an optically-detectable change.

A number of patents, discussed below, disclose devices for diluting and/or analyzing biological fluid samples. These devices include valve-like designs to control the flow of the sample.

U.S. Pat. No. 4,426,451, issued on Jan. 17, 1984 to Columbus, discloses a multi-zone fluidic device that has pressure-actuatable means for controlling the flow of fluid between the zones. His device makes use of pressure balances on a liquid meniscus at the interface between a first zone and a second zone that has a different cross section. When both the first and second zones are at atmospheric pressure, surface tension creates a back pressure that stops the liquid meniscus from proceeding from the first zone to the second. The configuration of this interface or "stop junction" is such that the liquid flows into the second zone only upon application of an externally generated pressure to the liquid in the first zone that is sufficient to push the meniscus into the second zone.

U.S. Pat. No. 4,868,129, issued on Sep. 19, 1989 to Gibbons et al., discloses that the back pressure in a stop junction can be overcome by hydrostatic pressure on the liquid in the first zone, for example by having a column of fluid in the first zone.

U.S. Pat. No. 5,230,866, issued on Jul. 27, 1993 to Shartle et al., discloses a fluidic device with multiple stop junctions in which the surface tension-induced back pressure at the stop junction is augmented; for example, by trapping and compressing gas in the second zone. The compressed gas can then be vented before applying additional hydrostatic pressure to the first zone to cause fluid to flow into the second zone. By varying the back pressure of multiple stop junctions in parallel, "rupture junctions" can be formed, having lower maximum back pressure.

U.S. Pat. No. 5,472,603, issued on Dec. 5, 1995 to Schembri (see also U.S. Pat. No. 5,627,041), discloses using centrifugal force to overcome the back pressure in a stop junction. When flow stops, the first zone is at atmospheric pressure plus a centrifugally generated pressure that is less than the pressure required to overcome the back pressure. The second zone is at atmospheric pressure. To resume flow, additional centrifugal pressure is applied to the first zone, overcoming the meniscus back pressure. The second zone remains at atmospheric pressure.

European Patent Application EP 0 803 288, of Naka et al., published on Oct. 29, 1997, discloses a device and method for analyzing a sample that includes drawing the sample into the device by suction, then reacting the sample with a reagent in an analytical section. Analysis is done by optical or electrochemical means. In alternate embodiments, there are multiple analytical sections and/or a bypass channel. The flow among these sections is balanced without using stop junctions.

U.S. Pat. No. 5,700,695, issued on Dec. 23, 1997 to Yassinzadeh et al., discloses an apparatus for collecting and manipulating a biological fluid that uses a "thermal pressure chamber" to provide the driving force for moving the sample through the apparatus.

U.S. Pat. No. 5,736,404, issued on Apr. 7, 1998, to Yassinzadeh et al., discloses a method for determining the coagulation time of a blood sample that involves causing an end of the sample to oscillate within a passageway. The oscillating motion is caused by alternately increasing and decreasing the pressure on the sample.

EP 0 922 954 A2 discloses a method for recognizing the presence of sample fluid on a test strip by monitoring the first and second derivatives of a parameter, such as reflectance from a mixture of the fluid and a reagent.

SUMMARY OF THE INVENTION

The present invention provides a method for initiating the measurement of an analyte concentration or property of a biological fluid that exhibits a "rouleaux" realignment. "Rouleaux formation" refers to the stacking of red blood cells, which permits a distinctive optical signature for such a fluid, typically whole blood. The method comprises
  a) providing a meter that measures the analyte concentration or a physical property of a blood sample on a fluidic diagnostic device,
  b) inserting into the meter the device, comprising
    (i) a sample port for introducing a sample of the biological fluid into the device,
    (ii) a measurement area, in which the analyte concentration or physical property is measured,
    (iii) a channel, having a first end and a second end, to provide a fluidic path from the sample port at the first end to the measurement area,
  c) applying the biological fluid sample to the sample port,
  d) illuminating the sample port and monitoring the light scattered from the sample over a predetermined period of time, and
  e) measuring the analyte concentration or physical property only if, during that time period, the scattered light has first increased abruptly, then decreased, whereby the meter will make the measurement only if the biological fluid is whole blood.

In another embodiment, the method of the present invention validates a measurement of an analyte concentration or property of a biological fluid only if it comprises whole blood. The method comprises
  a) providing a meter that measures the analyte concentration or physical property of a blood sample on a fluidic diagnostic device,
  b) inserting into the meter the device, comprising
    (i) a sample port for introducing a sample of the biological fluid into the device,
    (ii) a measurement area, in which the analyte concentration or physical property is measured,
    (iii) a channel, having a first end and a second end, to provide a fluidic path from the sample port at the first end to the measurement area,
  c) applying the biological fluid sample to the sample port,
  d) illuminating the sample port and monitoring the light scattered from the sample over a predetermined period of time,
  e) measuring the analyte concentration or physical property, and
  f) validating the measurement only if, during that time period, the scattered light has first increased abruptly, then decreased, whereby the meter will validate the measurement only if the biological fluid is whole blood.

In yet another embodiment, the present invention comprises a method for initiating a measurement of analyte concentration or a physical property of a biological fluid comprising
  a) providing a meter that measures the analyte concentration or physical property of a blood sample on a fluidic diagnostic device,
  b) inserting into the meter the device, comprising
    (i) a transparent sample port for introducing a sample of the biological fluid into the device,
    (ii) a measurement area, in which the analyte concentration or physical property is measured,
    (iii) a channel, having a first end and a second end, to provide a fluidic path from the sample port at the first end to the measurement area
  c) applying the biological fluid sample to the sample port,
  d) illuminating the sample port and monitoring the light transmitted through the sample over a predetermined period of time, and
  e) measuring the analyte concentration or physical property only if, during that time period, the transmitted light has first decreased abruptly, then increased, whereby the meter will make the measurement only if the biological fluid is whole blood.

The method of the present invention has broad application to various devices for measuring analyte concentrations and properties of blood, but it is particularly well adapted for measuring prothrombin time (PT time) of whole blood. In that case, the measurement area has a composition that catalyzes the blood clotting cascade.

DETAILED DESCRIPTION OF THE INVENTION

This invention relates a method of initiating a measurement in a fluidic device for analyzing certain biological fluids, particularly, whole blood. The device is generally of the type that, in combination with an appropriate meter, relates a physical parameter of blood, or an element of the blood, to an analyte concentration in the blood or to a property of the blood. Although a variety of physical parameters—e.g., electrical, magnetic, fluidic, or optical— can form the basis for the measurement, a change in optical parameters is a preferred basis, and the details that follow refer to an optical device. Similarly, the method can be adapted to a variety of device designs, including devices that involve capillary fill; however, we provide details for a particularly suitable device that includes a sample application area; a bladder, to create a suction force to draw the blood sample into the device; a measurement area, in which the sample may undergo a change in an optical parameter, such as light scattering; and a stop junction to precisely stop flow after filling the measurement area.
(Adapting the present method to other devices and for other measurements involves only routine experimentation.)

Preferably, the device is substantially transparent over the measurement area, so that the area can be illuminated by a light source on one side and the transmitted light measured on the opposite side. The measurement on the sample may be of a parameter that is not changing, but typically the sample undergoes a change in the measurement area, and the change in transmitted light is a measure of the analyte or fluid property of interest. Alternatively, light that is scattered from a fluid sample or light that passes through the sample and is reflected back through a second time (by a reflector on that opposite side) can be detected by a detector on the same side as the light source.

This type of device is suitable for a variety of analytical tests of blood, such as determining biochemical or hematological characteristics, or measuring the concentration of proteins, hormones, carbohydrates, lipids, drugs, toxins, gases, electrolytes, etc. The procedures for performing these tests have been described in the literature. Among the tests, and where they are described, are the. following:

(1) Chromogenic Factor XIIa Assay (and other clotting factors as well): Rand, M. D. et al., Blood, 88, 3432 (1996).

(2) Factor X Assay: Bick, R. L. Disorders of Thrombosis and Hemostasis: Clinical and Laboratory Practice. Chicago, ASCP Press, 1992.

(3) DRVVT (Dilute Russells Viper Venom Test): Exner, T. et al., Blood Coag. Fibrinol., 1, 259 (1990).

(4) Immunonephelometric and Immunoturbidimetric Assays for Proteins: Whicher, J. T., CRC Crit. Rev. Clin Lab Sci. 18:213 (1983).

(5) TPA Assay: Mann, K. G., et al., Blood, 76, 755, (1990).; and Hartshorn, J. N. et al., Blood, 78, 833 (1991).

(6) APTT (Activated Partial Thromboplastin Time Assay): Proctor, R. R. and Rapaport, S. I. Amer. J. Clin. Path, 36, 212 (1961); Brandt, J. T. and Triplett, D. A. Amer. J. Clin. Path., 76, 530 (1981); and Kelsey, P. R. Thromb. Haemost. 52, 172 (1984).

(7) HbA1c Assay (Glycosylated Hemoglobin Assay): Nicol, D. J. et al., Clin. Chem. 29, 1694 (1983).

(8) Total Hemoglobin: Schneck et al., Clinical Chem., 32/33, 526 (1986); and U.S. Pat. No. 4,088,448.

(9) Factor Xa: Vinazzer, H., Proc. Symp. Dtsch. Ges. Klin. Chem., 203 (1977), ed. By Witt, I (10) Colorimetric Assay for Nitric Oxide: Schmidt, H. H., et al., Biochemica, 2, 22 (1995).

The present method is particularly well suited for use in a device for measuring blood-clotting time—"prothrombin time" or "PT time"—and details regarding such a device appear below. The modifications needed to adapt the method and device for applications such as those listed above require no more than routine experimentation.

Figure 1:
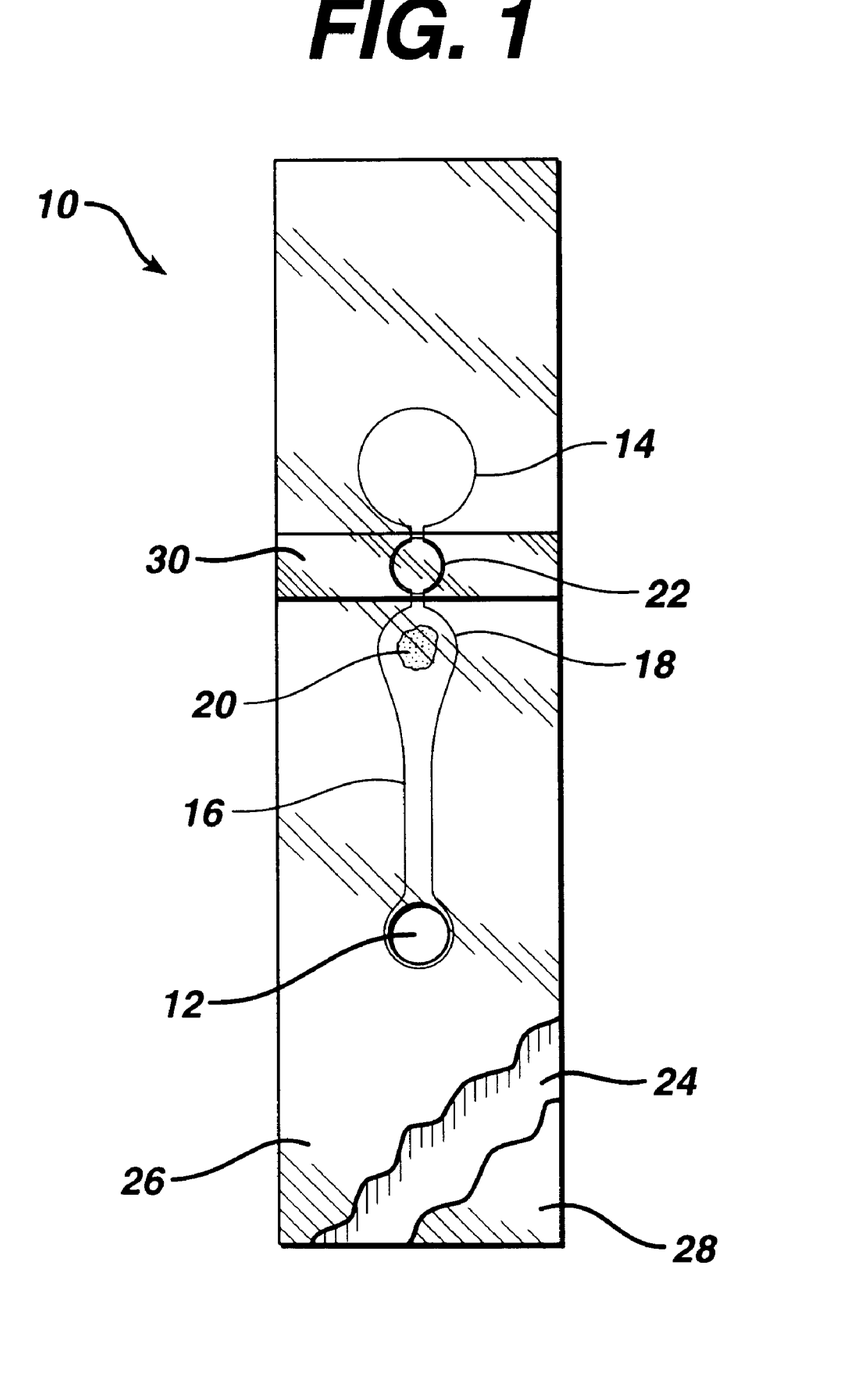
FIG. 1 is a plan view of a device that is suitable for use in the present invention.
Figure 2:
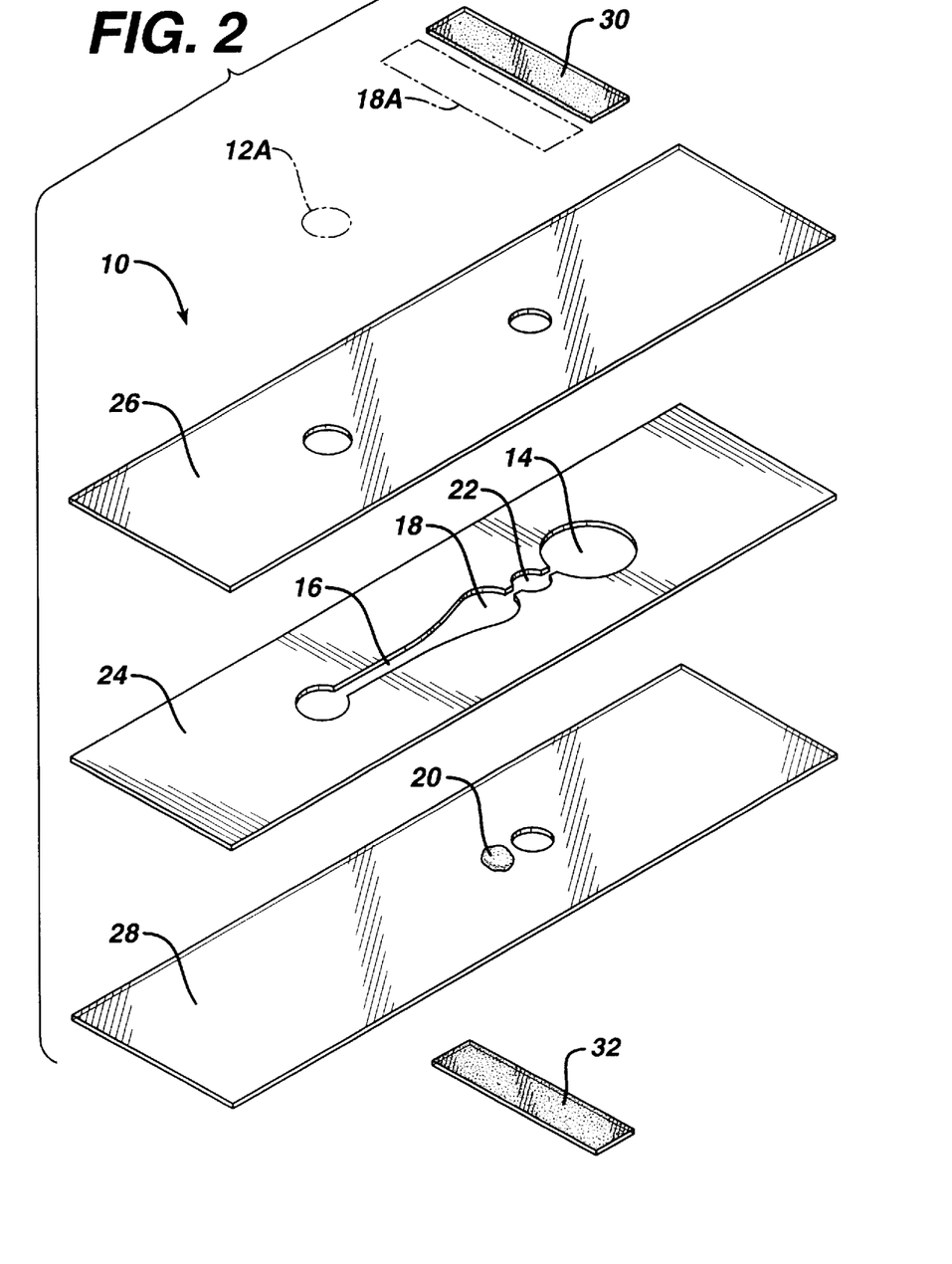
FIG. 2 is an exploded view of the device of FIG. 1.

FIG. 1 is a plan view of a device 10, suitable for use in the method of the present invention. FIG. 2 is an exploded view and FIG. 3 a perspective view of the device. Sample is applied to sample port 12 after bladder 14 has been compressed. Clearly, the region of layer 26 and/or layer 28 that adjoins the cutout for bladder 14 must be resilient, to permit bladder 14 to be compressed. Polyester of about 0.1 mm thickness has suitable resilience and springiness. Preferably, top layer 26 has a thickness of about 0.125 mm, bottom layer 28 about 0.100 mm. When the bladder is released, suction draws sample through channel 16 to measurement area 18, which preferably contains a reagent 20. In order to ensure that measurement area 18 can be filled with sample, the volume of bladder 14 is preferably at least about equal to the combined volume of channel 16 and measurement area 18. If measurement area 18 is to be illuminated from below, layer 28 must be transparent where it adjoins measurement area 18. For a PT test, reagent 20 contains thromboplastin that is free of bulking reagents normally found in lyophilized reagents.

Figure 3:
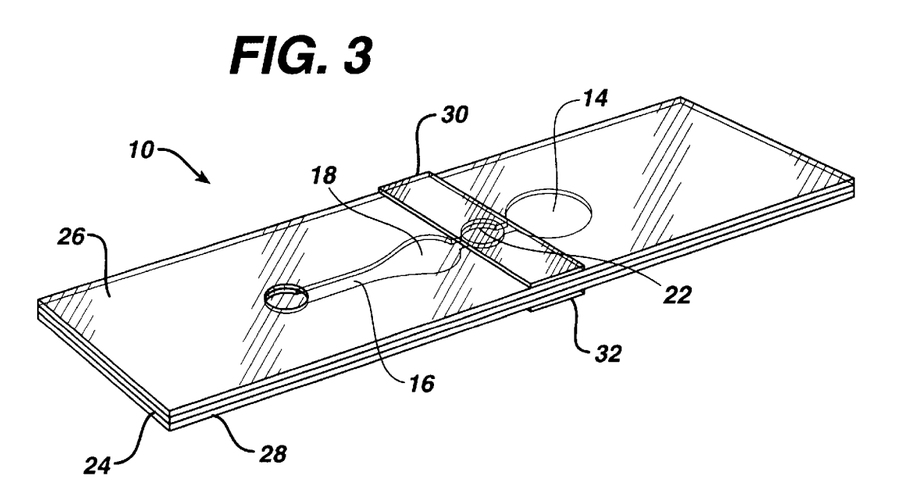
FIG. 3 is a perspective view of the device of FIG. 1.

As shown in FIGS. 1, 2, and 3, stop junction 22 adjoins bladder 14 and measurement area 18; however, a continuation of channel 16 may be on either or both sides of stop junction 22, separating the stop junction from measurement area 18 and/or bladder 14. When the sample reaches stop junction 22, sample flow stops. For PT measurements, it is important to stop the flow of sample as it reaches that point to permit reproducible rouleaux formation, which is an important step in monitoring blood clotting using the method described here. Note that rouleaux formation is reversible, and the rouleaux formed earlier, in the sample port, are eliminated as the blood travels through channel 16. The principle of operation of stop junctions is described in U.S. Pat. No. 5,230,866, incorporated herein by reference.

As shown in FIG. 2, all the above elements are formed by cutouts in intermediate layer 24, sandwiched between top layer 26 and bottom layer 28. Preferably, layer 24 is double-sided adhesive tape. Stop junction 22 is formed by an additional cutout in layer 26 and/or 28, aligned with the cutout in layer 24 and sealed with sealing layer 30 and/or 32. Preferably, as shown, the stop junction comprises cutouts in both layers 26 and 28, with sealing layers 30 and 32. Each cutout for stop junction 22 is at least as wide as channel 16. Also shown in FIG. 2 is an optional filter 12A to cover sample port 12. The filter may separate out red blood cells from a whole blood sample and/or may contain a reagent to interact with the blood to provide additional information. For reasons that will become clear below, the red blood cells must be visible from "below," so that the membrane must be transparent if it filters out red cells. Optional reflector 18A may be on, or adjacent to, a surface of layer 26 and positioned over measurement area 18. If the reflector is present, the device becomes a transflectance device.

Figures 4, 4A:
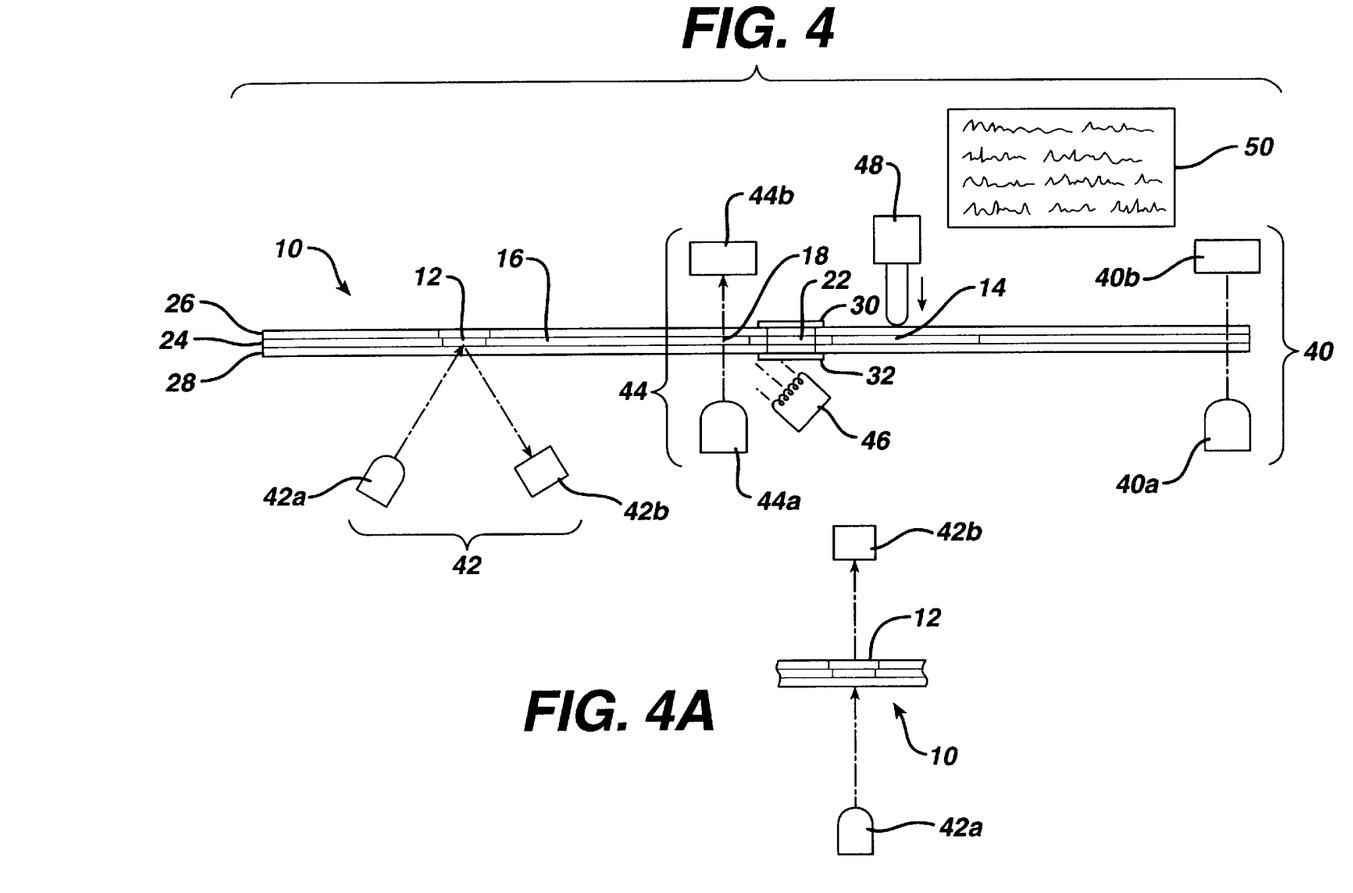
FIG. 4 is a schematic of a meter for use in the method of this invention.
FIG. 4A depicts an alternative embodiment of an element of the meter of FIG. 4.

The method of using the strip of FIGS. 1, 2, and 3 can be understood with reference to a schematic of the elements of a meter shown in FIG. 4. The first step the user performs is to turn on the meter, thereby energizing strip detector 40, sample detector 42, measurement system 44, and optional heater 46. The second step is to insert the strip. Preferably, the strip is not transparent over at least a part of its area, so that an inserted strip will block the illumination by LED 40a of detector 40b. (More preferably, the intermediate layer is formed of a non-transparent material, so that background light does not enter measurement system 44.) Detector 40b thereby senses that a strip has been inserted and triggers bladder actuator 48 to compress bladder 14. A meter display 50 then directs the user to apply a sample to sample port 12 as the third and last step the user must perform to initiate the measurement sequence.

It is important for the proper operation of the device to sense that an "appropriate" sample (i.e., whole blood) has been applied. Thus, the meter must not report a measurement if something other than a whole blood sample causes a change in the light detected by detector 42b. Such a change could result from the strip being moved, an object (e.g., a finger) being brought near the sample port, or, even, blood serum being applied to sample port 12. Each of these events could cause an erroneous result. To avoid this type of error, a preferred method of the present invention involves illuminating sample port 12 with LED 42a and measuring diffusely reflected (i.e., "scattered") light with detector 42b, positioned normal to the plane of strip 10. If a whole blood sample has been applied to sample port 12, the signal detected by 42b increases abruptly, because of scattering in the blood sample, then decreases, because the red cells begin to stack up like coins (rouleaux formation).

Figure 5:
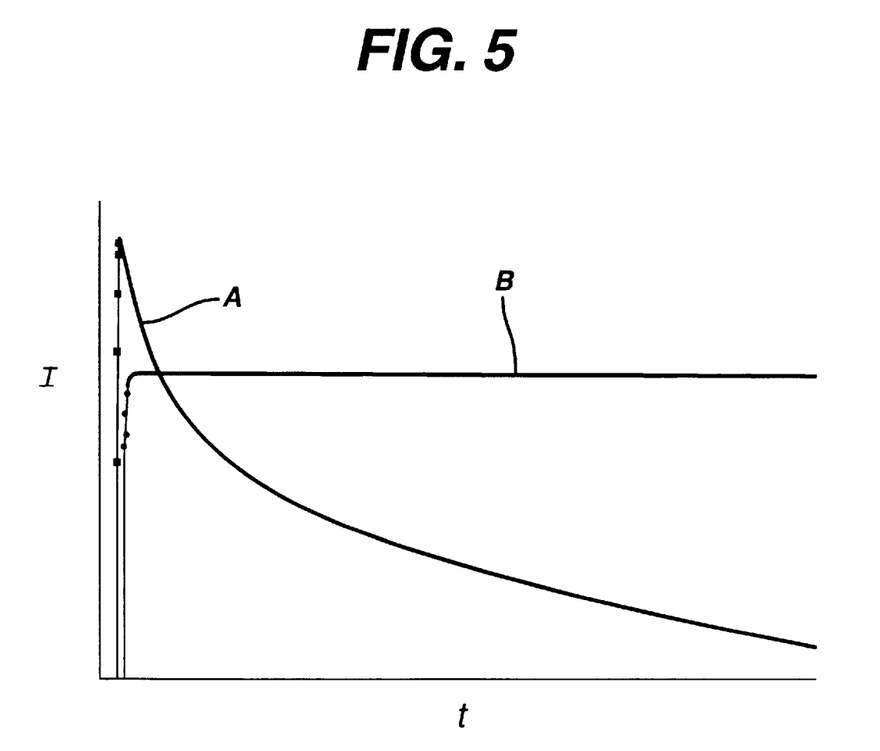
FIG. 5 is a graph of curves that identify a fluid as being, or not being, whole blood.

FIG. 5 depicts, as a function of time (t), this abrupt increase of scattered light intensity (I), followed by a decrease, which characterizes a blood sample—curve A. Also shown—curve B—is the dissimilar curve that characterizes a sample that is not whole blood.

In an alternative embodiment, shown in FIG. 4A, transmitted light is measured, instead of scattered light. In that case, the phenomenon of rouleaux formation causes the signal detected to decrease abruptly, then increase (i.e., the inverse of curve A).

The detector system 42 is programmed to first require the type of signal shown in FIG. 5 for whole blood, (curve A or its inverse, as the case may be), then cause actuator 48 to release bladder 14 to admit sample into channel 16. This, of course, requires a delay (preferably, at least about five seconds) as compared with simply admitting the sample without first determining whether it is whole blood. However, the delay in releasing bladder 14 does not substantially affect the readings described below. Releasing bladder 14 causes suction in channel 16 that draws sample through measurement area 18 to stop junction 22. Light from LED 44a passes through measurement area 18, and detector 44b monitors the light transmitted through the sample as it is clotting. When there are multiple measurement areas, measurement system 44 includes an LED/detector pair (like 44a and 44b) for each measurement area. Analysis of the transmitted light as a function of time (as described below) permits a calculation of the PT time, which is displayed on the meter display 50. Preferably, sample temperature is maintained at about 37° C. by heater 46.

In an alternative embodiment, bladder 14 is released in any case, but the analyte concentration/physical property measurement is only validated if the sample signature is detected by detector 42. If the signature is not detected, the user sees an error signal on display 50.

Figure 6:
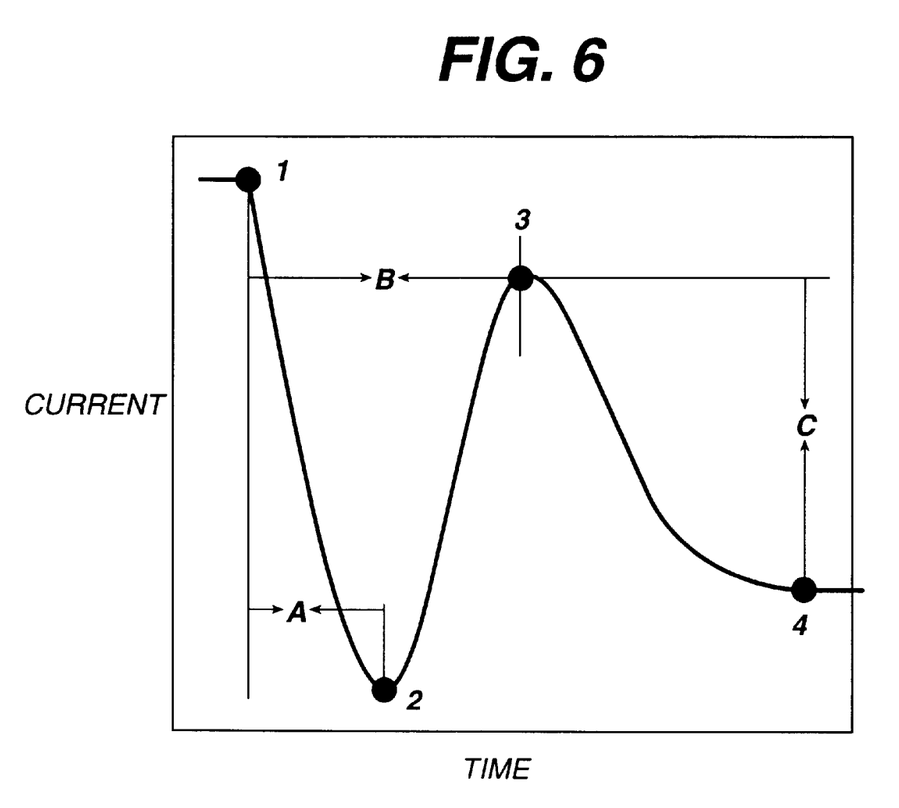
FIG. 6 is a graph of data that is used to determine PT time, using the meter of FIG. 4.

FIG. 6 depicts a typical "clot signature" curve in which the current from detector 44b is plotted as a function of time. Blood is first detected in the measurement area by 44b at time 1. In the time interval A, between points 1 and 2, the blood fills the measurement area. The reduction in current during that time interval is due to light scattered by red cells and is thus an approximate measure of the hematocrit. At point 2, sample has filled the measurement area and is at rest, its movement having been stopped by the stop junction. Rouleaux formation then allows increasing light transmission through the sample (and less scattering) in the time interval between points 2 and 3. At point 3, clot formation ends rouleaux formation and transmission through the sample reaches a maximum. The PT time can be calculated from the interval B between points 1 and 3 or between 2 and 3. Thereafter, blood changes state from liquid to a semi-solid gel, with a corresponding reduction in light transmission. The reduction in current C between the maximum 3 and endpoint 4 correlates with fibrinogen in the sample.

The device pictured in FIG. 2 and described above is preferably formed by laminating thermoplastic sheets 26 and 28 to a thermoplastic intermediate layer 24 that has adhesive on both of its surfaces. The cutouts that form the elements shown in FIG. 1 may be formed, for example, by laser- or die-cutting of layers 24, 26, and 28. Alternatively, the device can be formed of molded plastic. Preferably, the surface of sheet 28 is hydrophilic. (Film 9962, available from 3M, St. Paul, Minn.) However, the surfaces do not need to be hydrophilic, because the sample fluid will fill the device without capillary forces. Thus, sheets 26 and 28 may be untreated polyester or other thermoplastic sheet, well known in the art. Similarly, since gravity is not involved in filling, the device can be used in any orientation. Unlike capillary fill devices that have vent holes through which sample could leak, the present device vents through the sample port before sample is applied, which means that the part of the strip that is first inserted into the meter is without an opening, reducing the risk of contamination.

Figure 7:
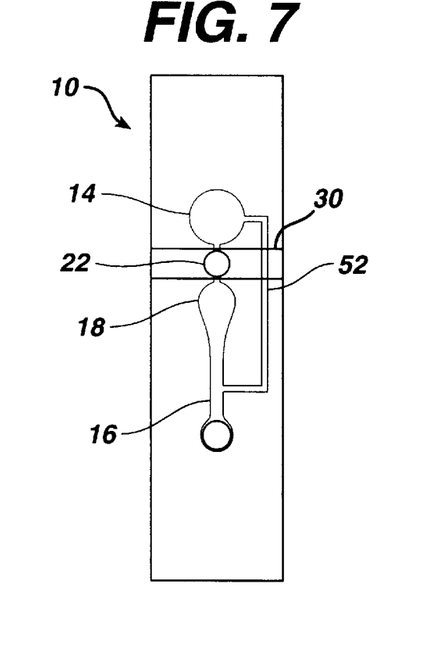
FIG. 7 is a plan view of an alternative embodiment of the device of FIG. 1.

FIG. 7 is a plan view of another embodiment of a device that is suitable for use with the method of the present invention, in which the device includes a bypass channel 52 that connects channel 16 with bladder 14. The function and operation of the bypass channel can be understood by referring to FIGS. 7A, 7B, and 7C, which depict a time sequence during which a sample is drawn into device 10 for the measurement.

Figure 7A:
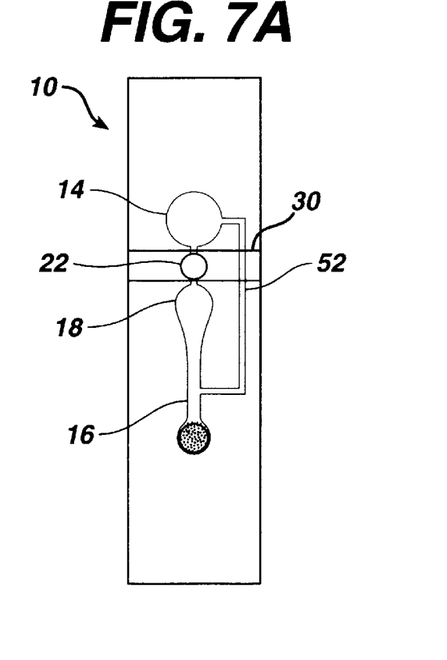
FIGS. 7A, 7B, and 7C depict a time sequence during which a sample is admitted to the device of FIG. 7.

FIG. 7A depicts the situation after a user has applied a sample to the strip, while bladder 14 is compressed. This can be accomplished by applying one or more drops of blood. The sample remains there while the meter determines whether the sample comprises whole blood. If so, the bladder is decompressed.

Figure 7B:
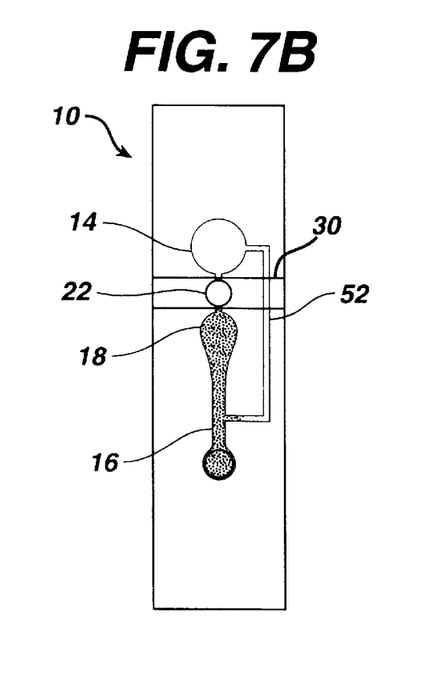

FIG. 7B depicts the situation after the bladder is decompressed. The resulting reduced pressure in the inlet channel 16 draws the sample initially into the measurement area 18. When the sample reaches stop junction 22, the sample encounters a back pressure that causes it to stop and causes additional sample to be drawn into the bypass channel.

Figure 7C:
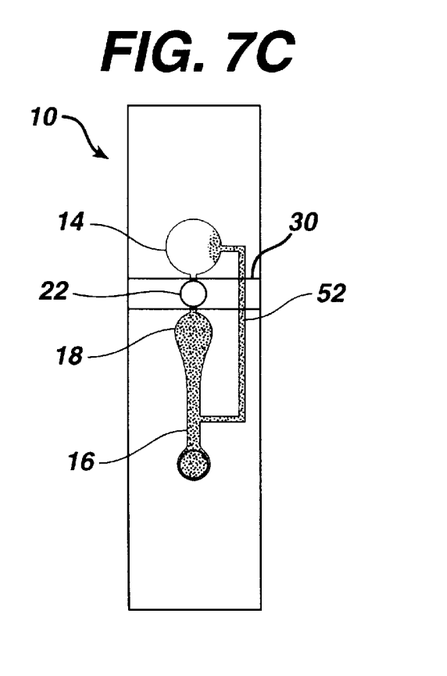

FIG. 7C depicts the situation when a reading is taken. Sample is at rest in measurement area 18. Sample also fills some, or (as shown) all, of channel 16.

Figure 8:
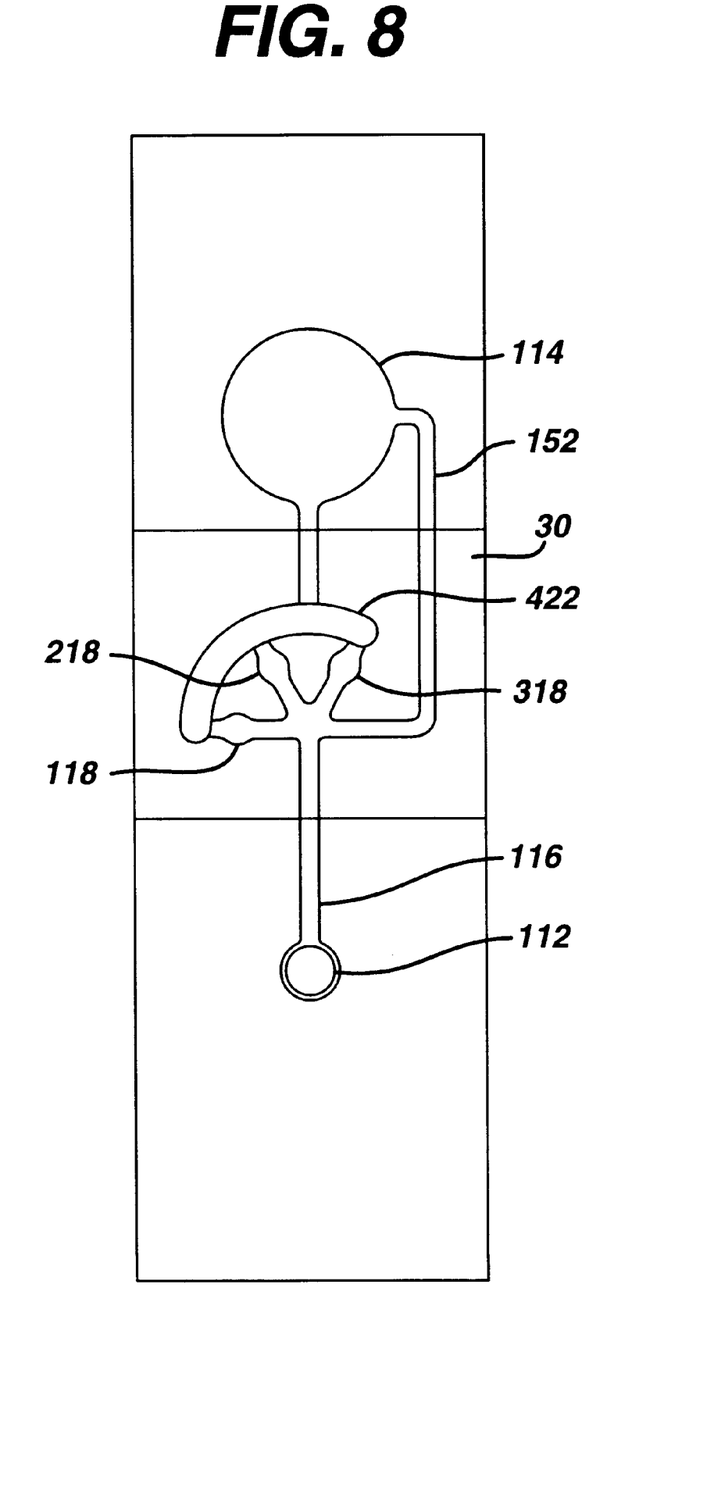
FIG. 8 is a schematic of a device that includes multiple measurement areas and a bypass channel.

FIG. 8 depicts a preferred embodiment of a device suitable for use with the present method. It is a multi-channel device that includes bypass channel 152. Bypass channel 152 serves a purpose in this device that is analogous to that served by bypass channel 52 in the device of FIG. 7, which was described above. Measurement area 118 contains thromboplastin. Preferably, measurement areas 218 and 318 contain controls, more preferably, the controls described below. Area 218 contains thromboplastin, bovine eluate, and recombinant Factor VIIa. The composition is selected to normalize the clotting time of a blood sample by counteracting the effect of an anticoagulant, such as warfarin. Measurement area 318 contains thromboplastin and bovine eluate alone, to partially overcome the effect of an anticoagulent. Thus, three measurements are made on the strip. PT time of the sample, the measurement of primary interest, is measured on area 118. However, that measurement is validated only when measurements on areas 218 and 318 yield results within a predetermined range. If either or both of these control measurements are outside the range, then a retest is indicated. Extended stop junction 122 stops flow in all three measurement areas.

The following examples demonstrate devices suitable for use in the method of the present invention, but are not intended to be in any way limiting.

EXAMPLE 1

A strip that is suitable for use in the method of this invention is made by first passing a double-sided adhesive tape (RX 675SLT, available from Scapa Tapes, Windsor, Conn.) sandwiched between two release liners into a laminating and rotary die-cutting converting system. The pattern shown in FIG. 7, with the exception of the stop junction, is cut through the top release liner and tape, but not through the bottom release liner, which is then removed as waste, along with the cutouts from the tape. Polyester film treated to be hydrophilic (3M9962, available from 3M, St. Paul, Minn.) is laminated to the exposed bottom side of the tape. Reagent (thromboplastin, available from Ortho Clinical Diagnostics, Raritan, N.J.) is then printed onto the reagent area (18) of the polyester film by bubble jet printing, using printing heads 51612A, from Hewlett Packard, Corvallis, Oreg. A sample port is cut in untreated polyester film (AR1235, available from Adhesives Research, Glen Rock, Pa.) and then laminated, in register, to the top of the double-sided tape (after removing the release layer). A die then cuts the stop junction through the three layers of the sandwich. Finally, strips of single-sided adhesive tape (MSX4841, available from 3M, St. Paul, Minn.) are applied to the outside of the polyester layers to seal the stop junction.

EXAMPLE 2

A procedure that is similar to the one described in Example 1 is followed to make a strip of the type depicted in FIG. 8. Reagent that is bubble-jet printed onto areas 118P, 218P, and 318P is, respectively, thromboplastin; thromboplastin, bovine eluate, and recombinant Factor VIIa; and thromboplastin and bovine eluate alone. The bovine eluate (plasma barium citrate bovine eluate) is available from Haemotologic Technologies, Burlington, Vt.; and recombinant Factor VIIa from American Diagnostica, Greenwich, Conn.

Measurements made on a whole blood sample using the strip of this Example yield a curve of the type shown in FIG. 6 for each of the measurement areas. The data from the curves for the controls (measurement areas 218P and 318P) are used to qualify the data from the curve for measurement area 118P. As a result, the PT time can be determined more reliably than can be done with a strip having a single measurement area.

The invention having been fully described, it will be apparent to one of ordinary skill in the art that many modifications and changes. may be made to it without departing from the spirit and scope of the present invention.

I claim:

1. A method for initiating a measurement of analyte concentration or a physical property of a biological fluid comprising:
   a) providing a meter that measures the analyte concentration or physical property of a blood sample on a fluidic diagnostic device,
   b) inserting into the meter the device, comprising
      (i) a sample port for introducing a sample of the biological fluid into the device,
      (ii) a measurement area, in which the analyte concentration or physical property is measured,
      (iii) a channel, having a first end and a second end, to provide a fluidic path from the sample port at the first end to the measurement area,
   c) applying the biological fluid sample to the sample port,
   d) illuminating the sample port and monitoring the light scattered from the sample over a predetermined period of time, and
   e) measuring the analyte concentration or physical property only if, during that time period, the scattered light has first increased abruptly, then decreased, whereby the meter will make the measurement only if the biological fluid is whole blood.

2. The method of claim 1 in which the predetermined time is at least about five seconds.

3. A method for validating a measurement of analyte concentration or a physical property of a biological fluid comprising:
   a) providing a meter that measures the analyte concentration or physical property of a blood sample on a fluidic diagnostic device,
   b) inserting into the meter the device, comprising
      (i) a sample port for introducing a sample of the biological fluid into the device,
      (ii) a measurement area, in which the analyte concentration or physical property is measured,
      (iii) a channel, having a first end and a second end, to provide a fluidic path from the sample port at the first end to the measurement area,
   c) applying the biological fluid sample to the sample port,
   d) illuminating the sample port and monitoring the light scattered from the sample over a predetermined period of time,
   e) measuring the analyte concentration or physical property, and
   f) validating the measurement only if, during that time period, the scattered light has first increased abruptly, then decreased, whereby the meter will validate the measurement only if the biological fluid is whole blood.

4. A method for initiating a measurement of analyte concentration or a physical property of a biological fluid comprising:
   a) providing a meter that measures the analyte concentration or physical property of a blood sample on a fluidic diagnostic device,
   b) inserting into the meter the device, comprising
      (i) a transparent sample port for introducing a sample of the biological fluid into the device,
      (ii) a measurement area, in which the analyte concentration or physical property is measured,
      (iii) a channel, having a first end and a second end, to provide a fluidic path from the sample port at the first end to the measurement area
   c) applying the biological fluid sample to the sample port,
   d) illuminating the sample port and monitoring the light transmitted through the sample over a predetermined period of time, and
   e) measuring the analyte concentration or physical property only if, during that time period, the light has first decreased abruptly, then increased, whereby the meter will make the measurement only if the biological fluid is whole blood.

5. The method of claim 4 in which the predetermined time is at least about five seconds.

* * * * *